United States Patent
O'Lenick, Jr.

(10) Patent No.: US 7,291,323 B1
(45) Date of Patent: Nov. 6, 2007

(54) SILICONE LUBRICATING AND CONDITIONING COMPOSITIONS

(76) Inventor: Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 758 days.

(21) Appl. No.: 10/746,641

(22) Filed: Dec. 29, 2003

(51) Int. Cl.
 *A61Q 5/12* (2006.01)
 *C07F 7/04* (2006.01)
 *C07F 7/08* (2006.01)
(52) U.S. Cl. .................... 424/70.12; 556/437; 514/880
(58) Field of Classification Search .................. 424/1, 424/70.12; 556/437; 514/880
See application file for complete search history.

(56) References Cited

U.S. PATENT DOCUMENTS

| 4,724,248 A | 2/1988 | Dexter et al. |
| 5,136,063 A | 8/1992 | O'Lenick et al. |
| 5,656,664 A * | 8/1997 | O'Lenick, Jr. .............. 514/552 |
| 2003/0003072 A1 * | 1/2003 | Hino et al. .............. 424/70.12 |

* cited by examiner

*Primary Examiner*—Sreeni Padmanabhan
*Assistant Examiner*—Kendra D. Carter

(57) ABSTRACT

The invention is directed to compositions that provide outstanding lubrication and conditioning to fibers. Key to the invention is the realization that the there must be (a) an alkoxylated silicone compound, and (b) a specific mono functional ester made from a capped polyoxyalkylene glycol compound. Combinations of these two specific materials properly chosen will result in lubricating and conditioning compositions that are effective and highly efficacious.

17 Claims, No Drawings

SILICONE LUBRICATING AND CONDITIONING COMPOSITIONS

CROSS-REFERENCE TO RELATED APPLICATIONS

No related applications.

STATEMENT REGARDING FEDERALLY SPONSORED RESEARCH OR DEVELOPMENT

No Federal Sponsorship

BACKGROUND OF THE INVENTION

For many years, there has been an industry desire to develop products that provide effective lubrication of fibers. These fibers include hair and a variety of textile fibers including cotton, rayon, nylon, and polyester. The need for an effective lubricant has grown recently with the popularity of microfibers, a very low denier fiber. The smaller the fiber, the greater the need for lubrication to prevent breakage during processing. As will become clear, the ability to provide effective lubrication was limited first by the chemistry of the lubrication compounds and then by the limitations of formulating these compounds into compositions.

By lubrication and conditioning, we mean the alteration of the fiber surface to provide a softer more appealing feel to the touch and at the same time provide lower friction values when the fibers pass over each other or when they pass over other objects, like metal parts or combs. In general, lubrication is the alteration of the surface to effect these changes. Conditioning is a type of lubrication in which the aesthetics of the lubricant are appealing. Hair is conditioned, fibers are generally lubricated, but both are related concepts.

Very early products aimed at lubricating and conditioning of fibers were simply oil or silicone emulsions. These composition included an oil phase (hydrocarbon, triglyceride or silicone oil), one of more emulsifiers and water. The difficulty with this approach was two fold. The first was that emulsions are metastable materials, and given enough time will separate. In addition, these emulsions are very sensitive to addition of additional surface active materials since the addition would alter the surfactant balance of the original emulsion and lead to splitting of the emulsion. That splitting would manifest itself by the formation of a water phase and an oil phase from a product that was homogeneous milk like liquid. This inability to add other ingredients limits the use of such products.

More recently, there has been a desire to make a soluble molecule that contains both silicone soluble groups and water soluble groups. These products are called silicone glycols. The products overcame the limitations related to emulsification, but in order to obtain a suitable level of water solubility, the lubrication and conditioning properties were significantly lessened. The compromised conditioning and lubrication properties, their inability to provide emulsification properties and their high cost limited the usefulness of such materials.

Several attempts were made to combine in one molecule water soluble groups, silicone soluble groups and oil soluble groups to make a truly functional lubricant for use in aqueous systems. One class of compounds are the silicone esters. Silicone esters have been known for years. U.S. Pat. No. 4,724,248 issued February 1988 to Dexter et al is the first patent to disclose silicone fatty esters, primarily for use in electrical systems. O'Lenick et al in U.S. Pat. No. 5,136,063 issued Aug. 4, 1992 later expanded the field. Still later, these materials were modified using specific triglycerides to maintain properties of the oil. These include U.S. Pat. No. 6,646,144 to Klein discloses cranberry based silicone esters and U.S. Pat. No. 6,630,180 to Klein discloses raspberry silicone esters.

While functional as skin care materials, these materials do not have the necessary properties to make a truly functional highly efficacious conditioner/lubricant. In fact, the recent approaches listed above indicate the desirability of making a compound that will provide the necessary functionality, rather than a specifically targeted composition. In other words, the recent trends in the art teach away from the use compositions.

Providing conditioning and lubrication to fiber is a complicated process, particularly when it is attempted with one compound. The process of conditioning or lubricating the fiber from aqueous solution includes several often-competitive processes including wetting of the fiber, and the deposition of the lubricant or conditioner onto the fiber. For example if one uses the silicone esters disclosed in U.S. Pat. No. 5,136,063, the specific ester chosen must have (a) water solubility, (b) wetting properties to allow for the uniform distribution of the molecule on the fiber, (c) ability to deposit rather than to wash off and (d) outstanding conditioning effects. Unfortunately, the selection of a molecule that has all properties has been elusive. This is because the optimization of one property is achieved at the expense of another. If one wants to improve water solubility one can add a lager water soluble group. This would decrease wetting, minimize deposition, increase wash off and lower conditioning effectiveness.

In order to attempt to overcome these problems, we looked at making compositions, containing one silicone molecule and an added surface active agent. The concept was to make a composition that would allow various processes to go on simultaneously, with minimal interferences one to the other. Many approaches simply did not work due to interactions between the compounds and interferences in the various processes.

BRIEF SUMMARY OF THE INVENTION

The present invention is directed to compositions that surprisingly provide outstanding lubrication and conditioning to fibers. Key to the invention is the realization that the there must be (a) an alkoxylated silicone compound, and (b) a specific mono functional ester made from a capped polyoxyalkylene glycol compound. As will become clear from the disclosure, these two specific materials properly chosen will result in lubricating and conditioning compositions that are effective and highly efficacious.

DETAILED DESCRIPTION OF THE INVENTION

The present invention is directed to a composition the composition which comprises:

(a) a silicone polymer conforming to the following structure;

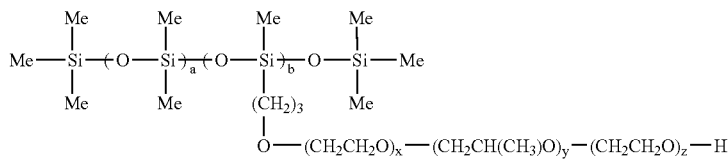

wherein
Me is methyl;
a is an integer ranging from 0 to 200;
b is an integer ranging from 1 to 20;
x, y and z are integers independently ranging from 0 to 20, with the proviso that x+y+z be greater than 5;
(b) a monofunctional polyoxyalkylene glycol ester conforming to the following structure;

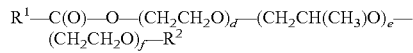

wherein:
$R^1$ is alkyl having 7 to 33 carbon atoms, and may be saturated or unsaturated, branched or linear;
$R^2$ is lower alkyl having one to four carbon atoms and may be saturated or unsaturated, branched or linear;

d, e, and f are integers independently ranging from 0 to 20, with the proviso that d+e+f be greater than 5.

An additional aspect of the present invention is a process for treating hair with compositions of the present invention, which comprise contacting the hair with an effective conditioning concentration of the following composition:
(a) a silicone polymer conforming to the following structure;

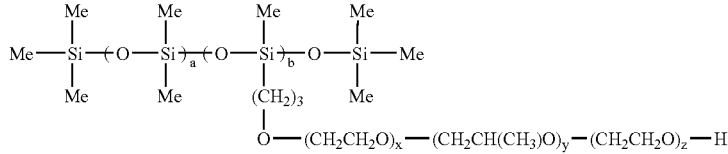

wherein
Me is methyl;
a is an integer ranging from 0 to 200;
b is an integer ranging from 1 to 20;
x, y and z are integers independently ranging from 0 to 20, with the proviso that x+y+z be greater than 5;
(b) a monofunctional polyoxyalkylene glycol ester conforming to the following structure;

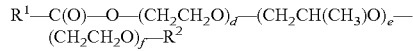

wherein:
$R^1$ is alkyl having 7 to 33 carbon atoms, and may be saturated or unsaturated, branched or linear;
$R^2$ is lower alkyl having one to four carbon atoms and may be saturated or unsaturated, branched or linear;

d, e, and f are independently integers ranging from 0 to 20, with the proviso that d+e+f be greater than 5.

The effective conditioning concentration ranges from 0.1% by weight to 10.0% by weight.

The polyoxyalkylene glycol must be monofunctional in order to provide the wetting properties without interfering with deposition. The presence of di-ester in the composition both interferes with wetting and being a hydrophobic material, causes problems with deposition of the silicone.

The selection of the capped polyoxyethylene glycol results in only monoester. One of the reactions is represented below:

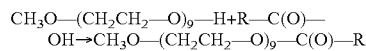

The resulting monoester is (a) water soluble, (b) a good wetting agent, allowing for the uniform distribution of the molecule on the fiber, (c) does not effect the ability of the silicone to deposit rather than to wash off and (d) provides outstanding conditioning effects.

It has always been assumed that one can make highly pure PEG monoesters by selecting the proper stiochiometric ratios. We find this is not the case. The resulting ester is not monoester, but a mixture. This mixture results from a direct result of the fact that there is a lack of regiospecificity between the two hydroxyl groups in the polyoxyethylene glycol reactant. Simply put, there is no preference for the fatty acid to with a hydroxyl group that is on a monoester or a free polyoxyethylene glycol group.

If one considers the reaction, in which a mono functional lauric acid ester is desired using a standard polyoxyethylene glycol and lauric acid the following reaction occurs:

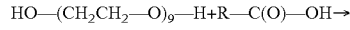

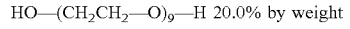

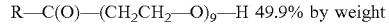

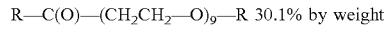

This mixture has profound negative effects upon the ability to make compositions that require high levels of mono-ester and concurrently low levels of the less water soluble di-ester.

The presence of 30% di-ester has dire effects upon the composition's performance. Since the monoester has 66% by weight polyoxyethylene, the di-ester is 50% by weight polyoxyethylene, the di-ester is far less water soluble than the mono-ester. It interferes with the wetting out of the fiber and the deposition of the silicone on the fiber.

PREFERRED EMBODIMENT

In a preferred embodiment $R^2$ is —$CH_3$.
In a preferred embodiment $R^2$ is —$(CH_2)_3CH_3$.
In a preferred embodiment, $R^1$ is alkyl having between 15 and 23 carbon atoms.
In a preferred embodiment, $R^1$ is alkyl having between 17 and 21 carbon atoms.
In a preferred embodiment, a is an integer ranging from 1 to 20.
In a preferred embodiment, b is an integer ranging from 1 to 5.
In a preferred embodiment x+y+z is greater than 10
In a preferred embodiment y is 0.
In a preferred embodiment y is 1 to 20.
In a preferred embodiment d+e+f is greater than 8.

EXAMPLES RAW MATERIALS (a) Dimethicone Copolyols

The raw material silicone compounds of the current invention are commercially available from Siltech LLC, Dacula, Ga. They conform to the following structure;

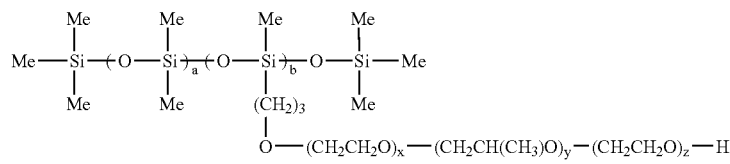

| Example | a | b | x | y | z |
|---|---|---|---|---|---|
| 1 | 1 | 0 | 0 | 0 | 5 |
| 2 | 4 | 0 | 0 | 0 | 5 |
| 3 | 4 | 8 | 5 | 4 | 5 |
| 4 | 4 | 10 | 20 | 20 | 20 |
| 5 | 4 | 100 | 20 | 0 | 20 |
| 6 | 4 | 20 | 5 | 10 | 20 |
| 7 | 10 | 150 | 10 | 15 | 10 |
| 8 | 10 | 200 | 20 | 5 | 20 |
| 9 | 15 | 10 | 0 | 10 | 20 |
| 10 | 20 | 1 | 10 | 10 | 10 |

(b) Monofunctional Polyoxyalkylene Glycol Compounds

These materials are commercially available from a variety of sources, including Siltech Corporation Toronto Canada. The values for d, e, and f were provided by Siltech and verified by nmr analysis. were

Example 11-19 Methyl Capped

These compounds conform to the following structure:

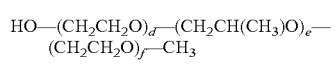

wherein;

d, e, and f are independently integers ranging from 0 to 20, with the proviso that d+e+f be greater than 5.

| Example | d | e | f |
|---|---|---|---|
| 11 | 0 | 0 | 5 |
| 12 | 0 | 5 | 0 |
| 13 | 10 | 1 | 5 |
| 14 | 20 | 20 | 20 |
| 15 | 5 | 5 | 5 |
| 16 | 10 | 0 | 0 |
| 17 | 20 | 0 | 20 |
| 18 | 5 | 10 | 10 |
| 19 | 23 | 0 | 0 |

Example 20-31 Butanol Capped

These compounds conform to the following structure:

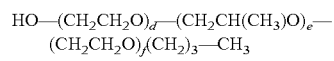

wherein;

d, e, and f are independently integers ranging from 0 to 20, with the proviso that d+e+f be greater than 5.

| Example | d | e | f |
|---|---|---|---|
| 20 | 0 | 5 | 0 |
| 21 | 5 | 0 | 0 |
| 22 | 20 | 20 | 20 |

| Example | d | e | f |
|---|---|---|---|
| 23 | 5 | 5 | 10 |
| 24 | 10 | 10 | 10 |
| 25 | 2 | 2 | 2 |
| 26 | 2 | 5 | 10 |
| 27 | 5 | 20 | 5 |
| 28 | 3 | 3 | 3 |
| 29 | 0 | 20 | 0 |
| 30 | 5 | 5 | 8 |
| 31 | 1 | 3 | 1 |

Preparation of Monofunctional Polyoxyalkylene Glycol Ester

The preparation of the esters useful as raw materials in the preparation of the compositions is as follows:

Fatty Acid Reaction:

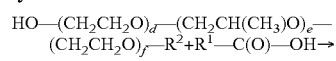

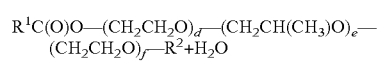

The fatty acids useful in the synthesis of compounds for the present invention conform to the following structure:

$$R^1-C(O)-OH$$

wherein;
$R^1$ is alkyl having 7 to 33 carbon atoms, and may be saturated or unsaturated, branched or linear.

| Example | R1 | Common Name | Formula |
|---|---|---|---|
| 32 | C7 | Caprylic acid | $C_8H_{16}O_2$ |
| 33 | C9 | Capric acid | $C_{10}H_{20}O_2$ |
| 34 | C11 | Lauric acid | $C_{12}H_{24}O_2$ |
| 35 | C11 | Lauroleic acid | $C_{12}H_{22}O_2$ |
| 36 | C13 | Myristic acid | $C_{14}H_{28}O_2$ |
| 37 | C14 | Myristoleic acid | $C_{14}H_{26}O_2$ |
| 38 | C15 | Palmitic acid | $C_{16}H_{32}O_2$ |
| 39 | C15 | Palmitoleic acid | $C_{16}H_{30}O_2$ |
| 40 | C17 | Stearic acid | $C_{18}H_{36}O_2$ |
| 41 | C17 | Oleic acid | $C_{18}H_{34}O_2$ |
| 42 | C17 | Linoleic acid | $C_{18}H_{32}O_2$ |

| Example | R1 | Common Name | Formula |
|---|---|---|---|
| 43 | C17 | Linolenic acid | $C_{18}H_{30}O_2$ |
| 44 | C19 | Arachidic acid | $C_{20}H_{40}O_2$ |
| 45 | C19 | Gadoleic acid | $C_{20}H_{38}O_2$ |
| 46 | C21 | Behenic acid | $C_{22}H_{44}O_2$ |
| 47 | C21 | Erucic acid | $C_{22}H_{42}O_2$ |
| 48 | C21 | Clupanodinic acid | $C_{22}H_{40}O_2$ |
| 49 | C23 | Lignoceric acid | $C_{24}H_{48}O_2$ |
| 50 | C26 | Cerotic acid | $C_{26}H_{52}O_2$ |
| 51 | C27 | Montanic acid | $C_{28}H_{56}O_2$ |
| 52 | C29 | Myricic acid | $C_{30}H_{60}O_2$ |
| 53 | C31 | Lacceroic acid | $C_{32}H_{65}O_2$ |
| 54 | C33 | Geddic acid | $C_{34}H_{68}O_2$ |

Triglyceride Reaction:

Triglycerides are another source of alkyl group. These natural products can be substituted for fatty acids and the resulting product is identical, except glycerin is produced rather than water.

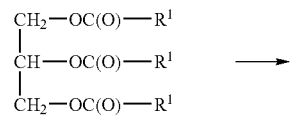
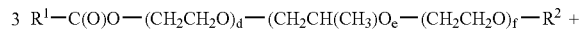
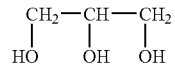

The glycerin is left in the product.

Nature has provided man with a large number of triglycerides. Examples are given below;

Carbon Number and Average $R^1$ Value

Triglycerides are classified by the source of the product (animal or plant), and by carbon number. Carbon number is the value obtained by multiplying the percentage of a component in a product by the number of carbon atoms in the component, then adding up all the components.

For example if an oil had the following composition:

| Component | % Weight |
|---|---|
| C16 | 20 |
| C18 | 20 |
| C18:1 | 20 |
| C20 | 40 |
| Total | 100 |

The carbon number calculation would be as follows:

| Component | (a) % Weight | (b) Carbon Atoms in Component | Calculation (a)*(b) |
|---|---|---|---|
| C16 | 20 | 16 | 3.2 |
| C18 | 20 | 18 | 3.6 |
| C18:1 | 20 | 18 | 3.6 |
| C20 | 40 | 20 | 8.0 |
| Total | 100 | | 18.4 |

Carbon number = 18.4

Average R1 is carbon number −1. This is because the C=O carbon is counted in the carbon number, but not in the $R^1$ definition.

Average $R^1$ = 17.4

There are several types of oils that have very similar carbon numbers. One can expect derivatives from oils having a very similar carbon number of unsaturation to have very similar, often identical functional properties. The choice of which of the many oils to choose in this instance depends upon the economics of the oil or the desire of the formulator to name the oil for label and marketing purposes.

| Example | Triglyceride | Average $R^1$ |
|---|---|---|
| 55 | Coconut Oil | 11.8 |
| 56 | Palm Kernel Oil | 12.3 |
| 57 | Babassu Oil | 12.4 |
| 58 | Sunflower oil | 15.0 |
| 59 | Palm oil | 16.1 |
| 60 | Apricot Kernel oil | 16.1 |
| 61 | Tallow | 16.3 |

| Example | Triglyceride | Average $R^1$ |
|---|---|---|
| 62 | Coca butter | 16.5 |
| 63 | Andiroba Oil | 16.5 |
| 64 | Mango Butter | 16.5 |
| 65 | Avacado oil | 16.6 |
| 66 | Cottonseed oil | 16.6 |
| 67 | Rice bran oil | 16.6 |
| 68 | Shea butter | 16.6 |
| 69 | Wheatgerm oil | 16.7 |
| 70 | Illipe butter | 16.7 |
| 71 | Corn oil | 16.8 |
| 72 | Olive oil | 16.8 |
| 73 | Poppyseed oil | 16.8 |
| 74 | Grape seed oil | 16.8 |
| 75 | Sesame oil | 16.8 |
| 76 | Sweet Amond oil | 16.9 |
| 77 | Hazelnut oil | 16.9 |
| 78 | Soybean oil | 16.9 |

-continued

| Example | Triglyceride | Average $R^1$ |
|---|---|---|
| 79 | Safflower oil | 16.9 |
| 80 | Hybrid safflower oil | 16.9 |
| 81 | Walnut oil | 16.9 |
| 82 | Canola oil | 16.9 |
| 83 | Peanut oil | 17.0 |

| Example | Triglyceride | Average $R^1$ |
|---|---|---|
| 84 | Kokhum Butter | 17.0 |
| 85 | Cupuacu Butter | 17.2 |
| 86 | Borgae oil | 16.8 |
| 87 | Evening primrose | 16.9 |
| 88 | Veronia oil | 16.9 |
| 89 | Ongokea oil | 17.0 |
| 90 | Castor oil | 17.0 |
| 91 | Meadowfoam oil | 19.5 |

General Process

Acid Process (Examples 92-114)

When the monofunctional polyoxyalkylene glycol ester is prepared using fatty acid, water is distilled off the reaction mass so the proper overhead including condensers is needed.

To the specified number of grams of the specified monofunctional polyoxyalkylene glycol (examples 11-31) is added the specified number of grams of the specified fatty acid (examples 32-54). The reaction can be run with or without catalyst. Stannous oxylate is added at 0.1% of the total batch weight. The reaction mass is heated to 180-200° C. with a nitrogen sparge. Nitrogen is applied to aid in removing the water formed and more importantly to maintain color of the product. The reaction progress is monitored by acid value, which reduces by 98% during the reaction. The product is cooled and used without additional purification.

| | Monofunctional polyoxyalkylene Glycol | | Acid | |
|---|---|---|---|---|
| Example | Example | Grams | Example | Grams |
| 92 | 11 | 252.0 | 32 | 130.0 |
| 93 | 12 | 327.0 | 33 | 156.0 |
| 94 | 13 | 751.0 | 34 | 180.0 |
| 95 | 14 | 1712.0 | 35 | 178.0 |
| 96 | 15 | 767.0 | 36 | 206.0 |
| 97 | 16 | 472.0 | 37 | 220.0 |
| 98 | 17 | 1792.0 | 38 | 225.0 |
| 99 | 18 | 1282.0 | 39 | 225.0 |
| 100 | 19 | 1044.0 | 40 | 256.0 |
| 101 | 20 | 369.0 | 41 | 230.0 |
| 102 | 21 | 294.0 | 42 | 230.0 |
| 103 | 22 | 3014.0 | 43 | 278.0 |
| 104 | 23 | 1029.0 | 44 | 288.0 |
| 105 | 24 | 1544.0 | 45 | 300.0 |
| 106 | 25 | 368.0 | 46 | 300.0 |
| 107 | 26 | 898.0 | 47 | 300.0 |
| 108 | 27 | 1694.0 | 48 | 300.0 |
| 109 | 28 | 515.0 | 49 | 330.0 |
| 110 | 29 | 192.0 | 50 | 356.0 |
| 111 | 30 | 941.0 | 51 | 382.0 |
| 112 | 31 | 339.0 | 52 | 410.0 |
| 113 | 31 | 339.0 | 53 | 430.0 |
| 114 | 30 | 941.0 | 54 | 450.0 |

Triglyceride Process (Examples 115-151)

When the monofunctional polyoxyalkylene glycol ester is prepared using triglyceride, glycerin is generated rather than water.

To the specified number of grams of the specified monofunctional polyoxyalkylene glycol (examples 11-31) is added the specified number of grams of the specified triglyceride (examples 55-91). The reaction can be run with or without catalyst. Stannous oxylate is added at 0.1% of the total batch weight. The reaction mass is heated to 180-200° C. with a nitrogen sparge. Nitrogen is applied to maintain color of the product. The reaction progress is monitored by glycerin concentration, which reduces by 98% during the reaction. The product is cooled and used without additional purification.

| | Monofunctional polyoxyalkylene Glycol | | Triglyceride | |
|---|---|---|---|---|
| Example | Example | Gram | Example | Grams |
| 115 | 11 | 252.0 | 55 | 200.0 |
| 116 | 12 | 327.0 | 56 | 200.0 |
| 117 | 13 | 751.0 | 57 | 200.0 |
| 118 | 14 | 1712.0 | 58 | 224.0 |
| 119 | 15 | 767.0 | 59 | 225.0 |
| 120 | 16 | 472.0 | 60 | 254.0 |
| 121 | 17 | 1792.0 | 61 | 258.0 |
| 122 | 18 | 1282.0 | 62 | 260.0 |
| 123 | 19 | 1044.0 | 63 | 260.0 |
| 124 | 20 | 369.0 | 64 | 260.0 |
| 125 | 21 | 294.0 | 65 | 260.0 |
| 126 | 22 | 3014.0 | 66 | 260.0 |
| 127 | 23 | 1029.0 | 67 | 260.0 |
| 128 | 24 | 1544.0 | 68 | 260.0 |
| 129 | 25 | 368.0 | 69 | 265.0 |
| 130 | 26 | 898.0 | 70 | 260.0 |
| 131 | 27 | 1694.0 | 71 | 260.0 |
| 132 | 28 | 515.0 | 72 | 255.0 |
| 133 | 29 | 192.0 | 73 | 260.0 |
| 134 | 30 | 941.0 | 74 | 250.0 |
| 135 | 31 | 339.0 | 75 | 260.0 |

| | Monofunctional polyoxyalkylene Glycol | | Triglyceride | |
|---|---|---|---|---|
| Example | Example | Grams | Example | Grams |
| 136 | 11 | 252.0 | 76 | 260.0 |
| 137 | 12 | 327.0 | 77 | 265.0 |
| 138 | 13 | 751.0 | 78 | 265.0 |
| 139 | 14 | 1712.0 | 79 | 265.0 |

-continued

| Example | Monofunctional polyoxyalkylene Glycol Example | Grams | Triglyceride Example | Grams |
|---|---|---|---|---|
| 140 | 15 | 767.0 | 80 | 265.0 |
| 141 | 16 | 472.0 | 81 | 265.0 |
| 142 | 17 | 1792.0 | 82 | 265.0 |
| 143 | 18 | 1282.0 | 83 | 265.0 |
| 144 | 19 | 1044.0 | 84 | 260.0 |
| 145 | 20 | 369.0 | 85 | 288.0 |
| 146 | 21 | 294.0 | 86 | 270.0 |
| 147 | 22 | 3014.0 | 87 | 260.0 |
| 148 | 23 | 1029.0 | 88 | 260.0 |
| 149 | 24 | 1544.0 | 89 | 280.0 |
| 150 | 25 | 368.0 | 90 | 255.0 |
| 151 | 26 | 898.0 | 91 | 290.0 |

Compositions of the Present Invention

Examples 152-211

The compositions of the present invention are prepared by blending the dimethicone copolyol and the monofunctional polyoxyalkylene ester together. Initially, the two components will not be clear when blended, but as the agitation continues, the mixture clears and is ready for use.

| Example | Dimethicone Copolyol Example | Grams | Monofunctional polyoxyalkylene Ester Example | Grams |
|---|---|---|---|---|
| 152 | 1 | 950.0 | 92 | 50.0 |
| 153 | 2 | 800.0 | 93 | 200.0 |
| 154 | 3 | 700.0 | 94 | 300.0 |
| 155 | 4 | 600.0 | 95 | 400.0 |
| 156 | 5 | 500.0 | 96 | 500.0 |
| 157 | 6 | 400.0 | 97 | 600.0 |
| 158 | 7 | 300.0 | 98 | 700.0 |
| 159 | 8 | 200.0 | 99 | 800.0 |
| 160 | 9 | 50.0 | 100 | 950.0 |
| 161 | 10 | 500.0 | 101 | 500.0 |
| 162 | 1 | 400.0 | 102 | 600.0 |
| 163 | 2 | 400.0 | 103 | 600.0 |
| 164 | 3 | 500.0 | 104 | 500.0 |

| Example | Dimethicone Copolyol Example | Grams | Monofunctional polyoxyalkylene Ester Example | Grams |
|---|---|---|---|---|
| 165 | 4 | 300.0 | 105 | 700.0 |
| 166 | 5 | 400.0 | 106 | 600.0 |
| 16 | 6 | 50.0 | 107 | 950.0 |
| 168 | 7 | 950.0 | 108 | 50.0 |
| 169 | 8 | 900.0 | 109 | 100.0 |
| 170 | 9 | 800.0 | 110 | 200.0 |
| 171 | 10 | 700.0 | 111 | 300.0 |
| 172 | 1 | 600.0 | 112 | 400.0 |
| 173 | 2 | 500.0 | 113 | 500.0 |
| 174 | 3 | 500.0 | 114 | 500.0 |
| 175 | 4 | 400.0 | 115 | 600.0 |
| 176 | 5 | 400.0 | 116 | 600.0 |
| 177 | 6 | 400.0 | 117 | 600.0 |
| 178 | 7 | 450.0 | 118 | 550.0 |
| 179 | 8 | 300.0 | 119 | 700.0 |

| Example | Dimethicone Copolyol Example | Grams | Monofunctional polyoxyalkylene Ester Example | Grams |
|---|---|---|---|---|
| 180 | 9 | 300.0 | 120 | 700.0 |
| 181 | 10 | 200.0 | 121 | 800.0 |
| 812 | 1 | 50.0 | 122 | 950.0 |
| 183 | 2 | 900.0 | 123 | 100.0 |
| 184 | 3 | 800.0 | 124 | 200.0 |

| Example | Dimethicone Copolyol Example | Grams | Monofunctional polyoxyalkylene Ester Example | Grams |
|---|---|---|---|---|
| 185 | 4 | 700.0 | 125 | 300.0 |
| 186 | 5 | 600.0 | 126 | 400.0 |
| 187 | 6 | 500.0 | 127 | 500.0 |
| 188 | 7 | 500.0 | 128 | 500.0 |
| 189 | 8 | 500.0 | 129 | 500.0 |
| 190 | 9 | 450.0 | 130 | 550.0 |
| 191 | 10 | 450.0 | 131 | 550.0 |
| 192 | 1 | 400.0 | 132 | 600.0 |
| 193 | 2 | 400.0 | 133 | 600.0 |
| 194 | 3 | 400.0 | 134 | 600.0 |
| 195 | 4 | 500.0 | 135 | 500.0 |
| 196 | 5 | 300.0 | 136 | 700.0 |
| 197 | 6 | 300.0 | 137 | 700.0 |
| 198 | 7 | 300.0 | 138 | 700.0 |
| 199 | 8 | 400.0 | 139 | 600.0 |
| 200 | 9 | 500.0 | 140 | 500.0 |
| 201 | 10 | 500.0 | 141 | 500.0 |
| 202 | 1 | 500.0 | 142 | 500.0 |
| 203 | 2 | 500.0 | 143 | 500.0 |

| Example | Dimethicone Copolyol Example | Grams | Monofunctional polyoxyalkylene Ester Example | Grams |
|---|---|---|---|---|
| 204 | 3 | 400.0 | 144 | 600.0 |
| 205 | 4 | 300.0 | 145 | 700.0 |
| 206 | 5 | 200.0 | 146 | 800.0 |
| 207 | 6 | 50.0 | 147 | 950.0 |
| 208 | 7 | 200.0 | 148 | 800.0 |
| 209 | 8 | 200.0 | 149 | 800.0 |
| 210 | 9 | 400.0 | 150 | 600.0 |
| 211 | 10 | 300.0 | 151 | 700.0 |

Applications Examples

The products of the present invention can be easily added to water to make an aqueous solution. The ratio of the dimethicone copolyol to mono polyoxyalkylene glycol ester will have a dramatic effect upon functionality.

Generally, the products can be used at a ratio of between 5 and 95% by weight of the dimethicone copolyol, the remainder being the mono polyoxyalkylene glycol ester.

As the concentration of the dimethicone copolyol is increased from 5% the wet comb properties of the hair and the amount of friction of the fiber improve. The optimum is achieved between 40 and 60% by weight of the dimethicone copolyol.

As the $R^1$ value increases from C8 to C18, the wet comb properties of the hair and the amount of friction of the fiber improve. The optimum is achieved between C18. As one goes higher in the number of carbon atoms, the material becomes more sticky. One very interesting material is made from Meadowfoam seed oil, it has outstanding lubrication properties and is not sticky. We attribute this property to the unusual unsaturation pattern of Meadowfoam seed oil.

We also compared the blend with each of the components. The following results are typical:

| | Softness Rating (1-5 scale) (5 being best) | Description |
|---|---|---|
| Example 211 | 5 | Blend |
| Example 10 | 2 | Silicone alone |
| Example 151 | 1 | Mono polyoxyalkylene ester alone |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:

1. A composition, which comprises;
(a) a silicone polymer conforming to the following structure:

$$\text{Me}-\underset{\underset{\text{Me}}{|}}{\overset{\overset{\text{Me}}{|}}{\text{Si}}}-(\text{O}-\underset{\underset{\text{Me}}{|}}{\overset{\overset{\text{Me}}{|}}{\text{Si}}})_a-(\text{O}-\underset{\underset{(\text{CH}_2)_3}{|}}{\overset{\overset{\text{Me}}{|}}{\text{Si}}})_b-\text{O}-\underset{\underset{\text{Me}}{|}}{\overset{\overset{\text{Me}}{|}}{\text{Si}}}-\text{Me}$$

$$\text{O}-(\text{CH}_2\text{CH}_2\text{O})_x-(\text{CH}_2\text{CH}(\text{CH}_3)\text{O})_y-(\text{CH}_2\text{CH}_2\text{O})_z-\text{H}$$

wherein:
Me is methyl;
a is an integer ranging from 0 to 200;
b is an integer ranging from 1 to 20;
x, y and z are integers independently ranging from 0 to 20, with the proviso that x+y+z be greater than 5; and
(b) a monofunctional polyoxyalkylene glycol ester conforming to the following structure;

$$R^1-C(O)-O-(CH_2CH_2O)_d-(CH_2CH(CH_3)O)_e-(CH_2CH_2O)_f-R^2$$

wherein:
$R^1$ is alkyl having 7 to 33 carbon atoms, and may be saturated or unsaturated, branched or linear;
$R^2$ is selected from the group consisting of —$CH_3$ and —$(CH_2)_3CH_3$;
d, e, and f are independently integers ranging from 0 to 20, with the proviso that d+e+f be greater than 5.

2. A composition of claim 1 wherein $R^2$ is —$CH_3$.
3. A composition of claim 1 wherein $R^2$ is —$(CH_2)_3CH_3$.
4. A composition of claim 1 wherein $R^1$ is alkyl having between 15 and 23 carbon atoms.
5. A composition of claim 1 wherein a is an integer ranging from 1 to 20.
6. A composition of claim 1 wherein b is an integer ranging from 1 to 5.
7. A composition of claim 1 wherein y is 0.
8. A process for treating hair, which comprise contacting the hair with an effective conditioning concentration of the following composition according to claim 1:
(a) a silicone polymer conforming to the following structure;

$$\text{Me}-\underset{\underset{\text{Me}}{|}}{\overset{\overset{\text{Me}}{|}}{\text{Si}}}-(\text{O}-\underset{\underset{\text{Me}}{|}}{\overset{\overset{\text{Me}}{|}}{\text{Si}}})_a-(\text{O}-\underset{\underset{(\text{CH}_2)_3}{|}}{\overset{\overset{\text{Me}}{|}}{\text{Si}}})_b-\text{O}-\underset{\underset{\text{Me}}{|}}{\overset{\overset{\text{Me}}{|}}{\text{Si}}}-\text{Me}$$

$$\text{O}-(\text{CH}_2\text{CH}_2\text{O})_x-\text{CH}_2\text{CH}(\text{CH}_3)\text{O})_y-(\text{CH}_2\text{CH}_2\text{O})_z-\text{H}$$

wherein
Me is methyl;
a is an integer ranging from 0 to 200;
b is an integer ranging from 1 to 20;
x, y and z are integers independently ranging from 0 to 20, with the proviso that x+y+z be greater then 5 and;
(b) a monofunctional polyoxyalkylene glycol ester conforming to the following structure;

$$R^1-C(O)-O-(CH_2CH_2O)_d-(CH_2CH(CH_3)O)_e-(CH_2CH_2O)_f-R^2$$

wherein:
$R^1$ is alkyl having 7 to 33 carbon atoms, and may be saturated or unsaturated, branched or linear;
$R^2$ is selected from the group consisting of —$CH_3$ and —$(CH_2)_3CH_3$;
d, e, and f are independently integers ranging from 0 to 20, with the proviso that d+e+f be greater than 5.

9. A process of claim 8 wherein the effective conditioning concentration ranges from 0.1% by weight to 10.0% by weight.
10. A process of claim 8 wherein the concentration of silicone polymer ranges from 5% to 95% by weight and the concentration of monofunctional polyoxyalkylene glycol ester ranges from 95% by weight to 5% by weight.
11. A process of claim 8 wherein $R^2$ is —$CH_3$.
12. A process of claim 8 wherein $R^2$ is —$(CH_2)_3CH_3$.
13. A process of claim 8 wherein $R^1$ is alkyl having between 15 and 23 carbon atoms.
14. A process of claim 8 wherein a is an integer ranging from 1 to 20.
15. A process of claim 8 wherein b is an integer ranging from 1 to 5.
16. A process of claim 8 wherein y is 0.
17. A process of claim 8 wherein y is 1 to 20.

* * * * *